(12) United States Patent
Park et al.

(10) Patent No.: US 11,191,936 B2
(45) Date of Patent: Dec. 7, 2021

(54) COSMETIC DEVICE FOR IMPROVED TRANSDERMAL PERMEATION AND MANUFACTURING METHOD THEREOF

(71) Applicant: L'OREAL, Paris (FR)

(72) Inventors: Woo Ram Park, Kawasaki (JP); Shu Liu, Kawasaki (JP); Bradford Pistorio, Clark, NJ (US)

(73) Assignee: L'Oreal, Paris (FR)

( * ) Notice: Subject to any disclaimer, the term of this patent is extended or adjusted under 35 U.S.C. 154(b) by 24 days.

(21) Appl. No.: 16/323,480

(22) PCT Filed: Jun. 14, 2017

(86) PCT No.: PCT/JP2017/022764
§ 371 (c)(1),
(2) Date: Feb. 5, 2019

(87) PCT Pub. No.: WO2018/029992
PCT Pub. Date: Feb. 15, 2018

(65) Prior Publication Data
US 2019/0167962 A1    Jun. 6, 2019

(30) Foreign Application Priority Data

Aug. 9, 2016 (JP) .............................. JP2016-156330

(51) Int. Cl.
*A61M 37/00* (2006.01)
*A61N 2/00* (2006.01)

(52) U.S. Cl.
CPC ............. *A61M 37/00* (2013.01); *A61N 2/002* (2013.01); *A61M 2037/0007* (2013.01); *A61M 2207/00* (2013.01)

(58) Field of Classification Search
CPC ........................ A61M 2037/0007; A61N 2/06
See application file for complete search history.

(56) References Cited

U.S. PATENT DOCUMENTS 3,467,598 A * 9/1969 Kroenke ................. H01F 1/117
252/62.54
9,463,330 B2   10/2016 Edwards
(Continued)

FOREIGN PATENT DOCUMENTS

CN    101578914 A    11/2009
CN    101913855 A    12/2010
(Continued)

OTHER PUBLICATIONS

Chamberland, Marc; The Miraculous Space Efficiency of Honeycomb—Hexagons and the science of packing; 2015; Slate.com <<https://slate.com/technology/2015/07/hexagons-are-the-most-scientifically-efficient-packing-shape-as-bee-honeycomb-proves.html>> (Year: 2015).*

(Continued)

*Primary Examiner* — William R Carpenter
(74) *Attorney, Agent, or Firm* — Christensen O'Connor Johnson Kindness PLLC (57) ABSTRACT

Systems, devices, and methods are described for providing a cosmetic device configured to deliver an active component into a skin and a method for manufacturing such a cosmetic device. In an embodiment, the cosmetic device includes an anisotropic magnetic element located in or on the head part of the body and configured to generate a magnetic field which induces diamagnetism in the active component. In an embodiment, the anisotropic magnetic element has a honeycomb magnetization pattern.

12 Claims, 3 Drawing Sheets

(56) References Cited

U.S. PATENT DOCUMENTS

| | | | |
|---|---|---|---|
| 2006/0041182 A1 | 2/2006 | Forbes et al. | |
| 2007/0083237 A1* | 4/2007 | Teruel | A61N 2/004 607/1 |
| 2013/0096362 A1* | 4/2013 | Balzer | A61N 2/06 600/9 |
| 2013/0144109 A1* | 6/2013 | Edwards | A61M 37/00 600/9 |
| 2016/0089545 A1 | 3/2016 | Juluri et al. | |

FOREIGN PATENT DOCUMENTS

| | | | |
|---|---|---|---|
| CN | 102667602 A | 9/2012 | |
| JP | 59-130212 A | 7/1984 | |
| JP | S60-067326 U | 5/1985 | |
| JP | H07-037171 U | 7/1995 | |
| JP | 2010-529881 A | 9/2010 | |
| KR | 10-0938921 B1 | 1/2010 | |
| WO | 2009/135246 A1 | 11/2009 | |
| WO | 2011/156869 A1 | 12/2011 | |
| WO | 2013/110124 A1 | 8/2013 | |
| WO | 2015081256 A1 | 6/2015 | |
| WO | 2015/188223 A1 | 12/2015 | |
| WO | 2016044554 A1 | 3/2016 | |

OTHER PUBLICATIONS

International Search Report dated Oct. 5, 2017, issued in corresponding International Application No. PCT/JP2017/022764, filed Jun. 14, 2017, 4 pages.

Third Party Observation mailed Aug. 22, 2018, submitted in corresponding International Application No. PCT/JP2017/022764, filed Jun. 14, 2017, 3 pages.

Notice of Reasons for Rejection dated Jul. 13, 2020, issued in corresponding Japanese Application No. 2016-156330, filed Feb. 25, 2015, 8 pages.

Notice of Reasons for Rejection and Search Report with partial translation dated Aug. 25, 2020, issued in Chinese Application No. 201780047255.5, filed Jun. 14, 2017, 10 pages.

Chinese Office Action, dated Sep. 28, 2021, with English Translation, in corresponding Chinese Patent Application No. 201780047255.5, 7 pages.

* cited by examiner

COSMETIC DEVICE FOR IMPROVED TRANSDERMAL PERMEATION AND MANUFACTURING METHOD THEREOF

TECHNICAL FIELD

The present disclosure is related to a cosmetic device for improved transdermal permeation and a method for manufacturing such a cosmetic device.

BACKGROUND

Some kinds of cosmetic or pharmaceutical compositions such as skin-care compositions are intended to be applied to a skin by a hand (more precisely fingers or palms) or using an applicator. Polar and hydrophilic active components in the compositions are intended to be transdermally permeated deeper in the skin.

However, transdermal permeation of polar and hydrophilic active components is limited by the barrier property of stratum corneum (SC). Several chemical and physical permeation enhancement techniques have been explored to improve the transdermal delivery of poorly permeable molecules.

One candidate for active transdermal penetration is diamagnetism. Diamagnetism generally appears in most substances such as water, most small organic molecules. Diamagnetism is the property of a substance to induce a magnetic field in a direction opposite to an applied external magnetic field, and therefore, to be repelled by the applied external magnetic field. It is a promising non-invasive transdermal delivery for small organic molecules that are diamagnetic in nature.

One way to implement diamagnetism is to use an anisotropic magnetic array having alternating magnetic polarities. Basically, this requires N (North) and S (South) polarities to make a periodic magnetic pattern on the same surface. This anisotropic magnetic force then generates a non-polar oriented magnetic force on the surface from the array, it overall makes a diamagnetic repulsive field for active delivery.

For example, WO 2009/135246 discloses an anisotropic magnetic array of pairs of bar-shaped linear magnetic materials having alternating magnetic polarities. An insulating material is located between neighboring pairs of magnetic materials. The array of this document results in a linear magnetization pattern.

It can be understood that stronger magnetic forces generally generates stronger repulsion force with a target substance (i.e., active components). Thus, there remains a need for providing a more effective anisotropic magnetization pattern which results in a stronger magnetic force for improved transdermal permeation, compared with the conventional linear magnetization pattern.

SUMMARY

In an aspect, the present disclosure is directed to technologies and methodologies for realizing a stronger anisotropic magnetic force for a cosmetic device to improve the transdermal permeation of active components by providing an efficient magnetization pattern in a limited area.

The object is achieved by a cosmetic device for delivering an active component into a skin, comprising: a body including a handle part and a head part extending from the handle part; and an anisotropic magnetic element located in or on the head part of the body, the anisotropic magnetic element configured to generate a magnetic field and to induce diamagnetism in the active component; wherein the anisotropic magnetic element has a honeycomb magnetization pattern.

In one aspect, the honeycomb magnetization pattern may include a plurality of hexagonal magnetization zones in array, each hexagonal magnetization zone having either N polarity or S polarity.

In one aspect, the anisotropic magnetic element may include a neodymium rubber magnet.

In one aspect, the anisotropic magnetic element may have a magnetic flux density between about 50 gauss (G) and about 1500 gauss, preferably between about 100 gauss and about 300 gauss.

In one aspect, the head part of the body may include a cover for covering the anisotropic magnetic element within the head part of the body.

In an aspect, the present disclosure also relates to a method for delivering an active component into a skin, comprising: generating a magnetic field via an anisotropic magnetic element having a honeycomb magnetization pattern; and inducing diamagnetism in the active component.

In one aspect, generating the magnetic field via the anisotropic magnetic element having a honeycomb magnetization pattern includes magnetizing the anisotropic magnetic element such that the honeycomb magnetization pattern includes a plurality of hexagonal magnetization zones in array, each hexagonal magnetization zone has either N polarity or S polarity.

In one aspect, the plurality of hexagonal magnetization zones are magnetized by a magnetizer having an array of hexagonal magnetizing cores.

In one aspect, generating the magnetic field via the anisotropic magnetic element having a honeycomb magnetization pattern includes generating the magnetic field via an anisotropic magnetic element formed from a neodymium rubber magnet.

In one aspect, generating the magnetic field via the anisotropic magnetic element having a honeycomb magnetization pattern includes generating the magnetic field via an anisotropic magnetic element including a cover for covering the anisotropic magnetic element.

In an aspect, the present disclosure further relates to a method for manufacturing a cosmetic device for delivering an active component into a skin, comprising: providing a body comprising a handle part and a head part extending from the handle part; providing an anisotropic magnetic element configured to generate a magnetic field and to induce diamagnetism in the active component, the anisotropic magnetic element having a honeycomb magnetization pattern; and, attaching the anisotropic magnetic element to the head part of the body.

In one aspect, providing the anisotropic magnetic element includes magnetizing the anisotropic magnetic element such that the honeycomb magnetization pattern includes a plurality of hexagonal magnetization zones in array, each hexagonal magnetization zone has either N polarity or S polarity.

In one aspect, the plurality of hexagonal magnetization zones are magnetized by a magnetizer having an array of hexagonal magnetizing cores.

In one aspect, providing the anisotropic magnetic element includes forming the anisotropic magnetic element from a neodymium rubber magnet.

In one aspect, the method further comprises providing a cover for covering the anisotropic magnetic element.

Other objects, aspects, advantages, and features of the present invention will become apparent after reading the following detailed description of non-limiting embodiments together with the appended drawings.

DESCRIPTION OF EMBODIMENTS

Figure 1:
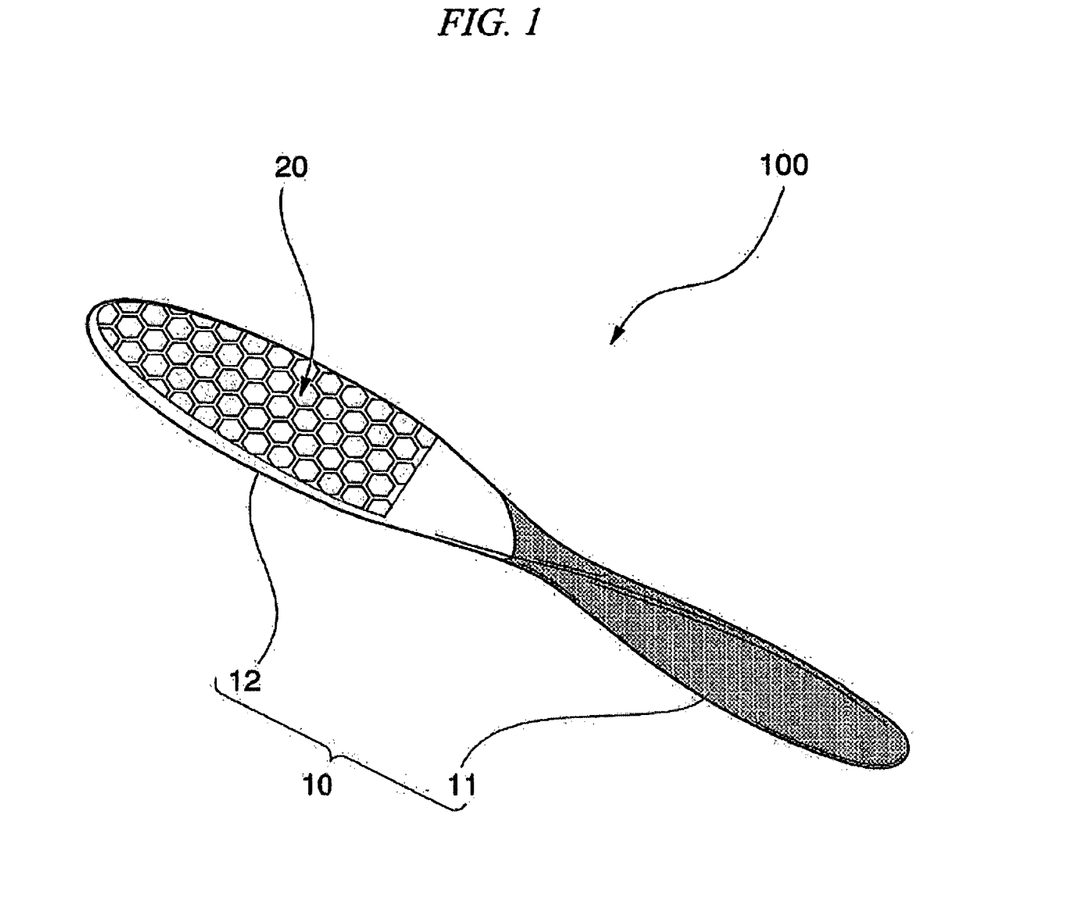
FIG. 1 is a schematic perspective view showing a cosmetic device according to an embodiment together with a honeycomb magnetization pattern.
Figure 2:
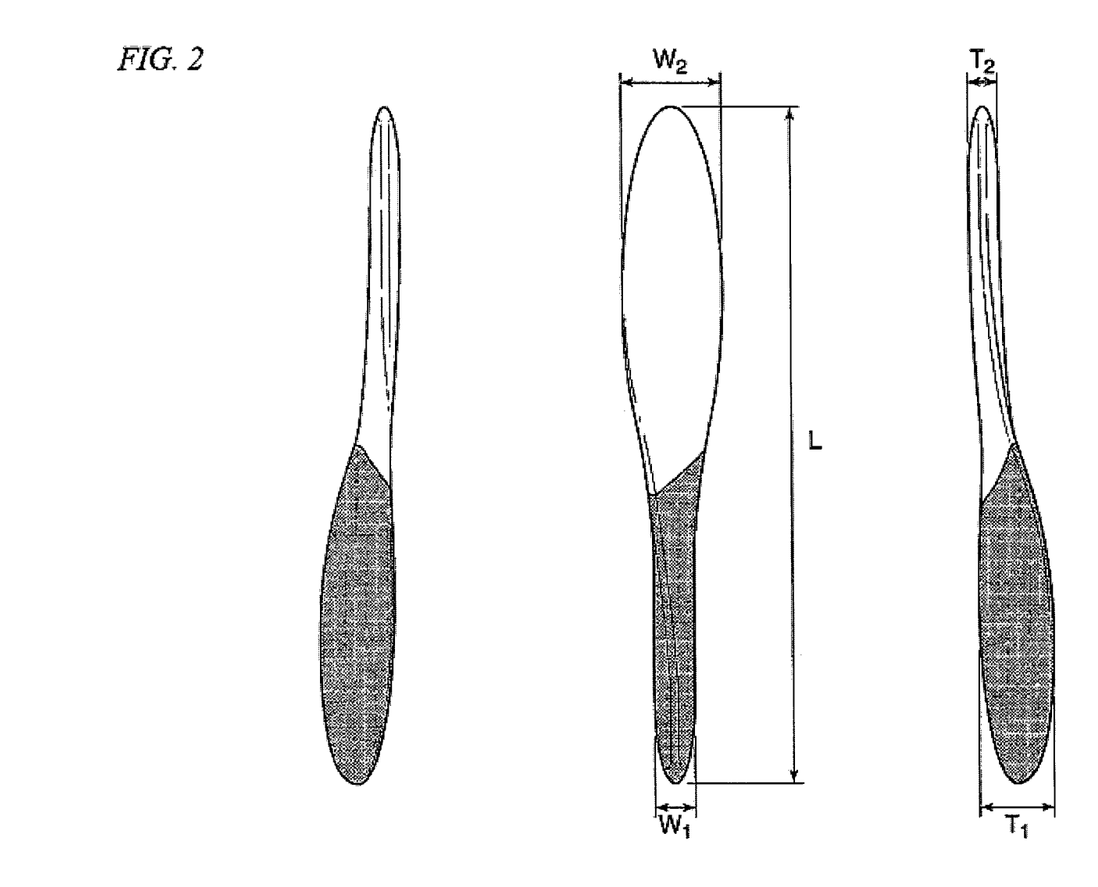
FIG. 2 shows a schematic top view and side views and of the cosmetic device of FIG. 1 together with characteristic dimensions.

FIG. 1 is a schematic perspective view showing a cosmetic device 100 according to an embodiment. FIG. 2 shows a schematic top view and schematic side views and of the cosmetic device 100. The cosmetic device 100 includes an elongate body 10 and an anisotropic magnetic element 20.

The body 10 comprises a handle part 11 and a head part 12 extending from the handle part 11.

The handle part 11 has any suitable shape for holding the cosmetic device 100 with fingers and/or a palm. For example, as shown in FIGS. 1 and 2, the handle part 11 may have a rounded bar shape.

The head part 12 extends from the handle part 11 and has a substantially flat surface. In one embodiment as shown in FIGS. 1 and 2, the head part 12 may torsionally extend from the handle part 11 so as to form a substantially flat surface. The substantially flat surface of the head part 12 may have a generally oval or elliptical shape. The edge of the head part 12 may be rounded.

In one embodiment, the head part 12 may include a cover for covering and surrounding the anisotropic magnetic element 20 within the head part 12. In this embodiment, the cover forms a part of the head part 12 such that the cover forms the substantially flat surface of the head part 12. In other words, the anisotropic magnetic element 20 is located within the head part 12. However, as further described below, the cover may be omitted.

The head part 12 is intended to contact a skin with the substantially flat surface thereof. Furthermore, the head part 12 may be configured to dip a composition from a composition container; apply it to a skin; and massage a skin so as to cause active components in the composition to penetrate into the skin due to the diamagnetic effect. In other words, the cosmetic device 100 including such a head part 12 may act as a spatula, an applicator, and a massager.

Referring to FIG. 2 showing a schematic top view and side views and of the cosmetic device 100 with characteristic dimensions, the body 10 has a length L. The length L of the body 10 may be between about 50 mm and about 100 mm (80 mm for example), depending on the applications (such as facial application, or bodily application). Correspondingly, the handle part 11 has a main width $W_1$ (i.e., maximum width in the handle part 11) and a main thickness $T_1$ (i.e., maximum thickness in the handle part 11). The head part 12 has a main width $W_2$ (i.e., maximum width in the head part 12) and a main thickness $T_2$ (i.e., maximum thickness in the head part 12). If the head part 12 has an elliptical flat surface, the main width $W_2$ of the head part 12 may corresponds to the minor axis of the ellipse. With regard to the handle part 11, the main width $W_1$ may be between about 3 mm and about 6 mm (4.8 mm for example), and the main thickness $T_1$ may be between about 6 mm and about 12 mm (9.2 mm for example). With regard to the head part 12, the main width $W_2$ may be between about 8 mm and 16 mm (13 mm for example), and the main thickness $T_2$ may be between about 3 mm and 8 mm (5.3 mm for example). However, the body 10 including the handle part 11 and the head part 12 may have any appropriate dimension without limitation.

In one embodiment, the handle part 11 and the head part 12 may be integrally formed by molding such as injection molding. In another embodiment, the handle part 11 and the head part 12 may be separately formed by molding, and then, joined together by adhesive for example.

The body 10 (i.e., the handle part 11, the head part 12, and the cover) may be formed from any suitable non-magnetic material such as resin. Non-limiting examples of resin include styrene-acrylonitrile (SAN) resin, acrylonitrile-butadiene-styrene (ABS) resin, polypropylene (PP) resin, polyester resin, elastomer resin, polyvinyl chloride. Non-magnetic metal materials such as aluminum or non-magnetic stainless steel may be also used for the material of the body 10.

The body 10 may be further surface-finished for aesthetic and/or protective purpose by means of coating or plating (such as electroless plating) of non-magnetic material, provided that such surface finishing does not affect the magnetic force from the anisotropic magnetic element 20.

In one embodiment, the anisotropic magnetic element 20 is located within the head part 12. For this purpose, as mentioned above, the cover as a part of the head part 12 may cover and surround the anisotropic magnetic element 20 within the head part 12. Alternatively, the anisotropic magnetic element 20 may be located on the head part 12 without a cover. In this alternative, the anisotropic magnetic element 20 may have the corresponding substantially flat surface which is intended to directly contact a skin.

The anisotropic magnetic element 20 may have a thickness between 0.1 mm to 2 mm (0.5 mm for example).

In one embodiment, the anisotropic magnetic element 20 may include a rubber magnet (also known as a bonded magnet) known in the art such as ferrite rubber magnet, rare-earth rubber magnet. The rare-earth rubber magnet includes, but not limited to, neodymium (NdFeB) rubber magnet, samarium-cobalt (SmCo) rubber magnet. Preferably, the rubber magnet may be a neodymium rubber magnet for its stronger magnetic force. The rubber magnet generally comprises magnet fine particles (such as ferrite or neodymium magnet fine particles), rubber material (or resin material) (such as nitrile rubber, silicone rubber) and appropriate additives (such as plasticizer, lubricant, cross-linker, anti-aging agent). The magnet fine particles are uniformly dispersed in the rubber material. The volume percentage of the magnet fine particles in the rubber magnet is within any appropriate range such as between about 10 vol. % and about 80 vol. %, preferably between about 60 vol. % and about 80 vol. % relative to the whole mixture. The size (i.e., particle diameter) of the magnet fine particle may be between about 0.5 μm and about 3.0 μm as is known in the art.

The rubber magnet may be formed by any method known in the art. For example, the rubber magnet may be formed by: uniformly mixing magnet fine particles with rubber material and additives to obtain the resultant mixture; and rolling the mixture to form a rubber magnet sheet. If an external magnetic field is applied during the rolling process, the magnet fine particles can be aligned such that the resultant rubber magnet sheet has a magnetic anisotropy, such as a magnetic anisotropy along a thickness direction of the sheet (i.e., along the direction which is normal to the main surface of the sheet). Then, the rubber magnet sheet may be cut in a desired shape so as to form the anisotropic magnetic element 20.

Figure 3:
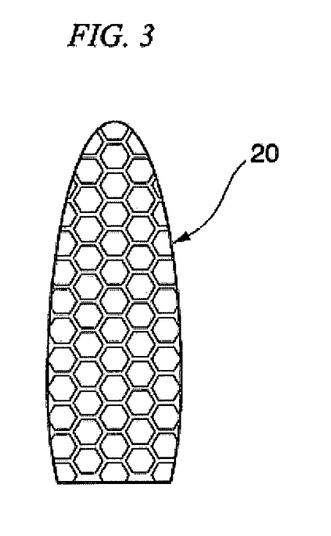
FIG. 3 is a schematic view of a honeycomb magnetization pattern which an anisotropic magnetic element according to an embodiment has.

Referring to FIGS. 1 and 3, the anisotropic magnetic element 20 exhibits a honeycomb anisotropic magnetization pattern. The honeycomb anisotropic magnetization pattern includes a plurality of regular hexagonal magnetization zones in array. The size of each hexagonal magnetization zone (typically, the length of one side of a regular hexagon) may be between about 1 mm and about 10 mm (3 mm for example). If the length of one side of a regular hexagon is about 3 mm, the surface area of a regular hexagon is equal to about 23.4 mm$^2$. Each hexagonal magnetization zone has either N (North) or S (South) polarity in a direction perpendicular to the main surface of the magnetic element 20.

In one embodiment, N polarities and S polarities alternate in each row of hexagonal magnetization zones. In this context, the term of "row" means a plurality of hexagonal magnetization zones whose sides are abutting each other. In this embodiment, two neighboring hexagonal magnetization zones in each row form a dipole pair.

In another embodiment, all hexagonal zones in one row of hexagonal zones have the same polarity while hexagonal zones in two neighboring rows have the opposite polarity.

However, each hexagonal zone can independently have either N or S polarity so as to enhance the anisotropic magnetic force. Naturally, the magnetic force makes a circular radius in the center, but this round type pattern makes many empty spaces between zones. On the contrary, the honeycomb pattern makes smaller gaps between zones to generate even stronger anisotropic magnetic forces.

Due to the above constitution of the anisotropic magnetic element 20, the anisotropic magnetic element 20 may have a higher magnetic flux density between about 50 gauss (G) and about 1500 gauss, preferably between about 100 and about 300 gauss (G), or above (such as about 500 G or above).

The anisotropic magnetic element 20 is magnetized by a magnetizer. In order to form the honeycomb magnetization pattern, the magnetizer has a hexagonal magnetizing core. Using the magnetizer, hexagonal zones can be magnetized one by one like stamping.

Figure 4:
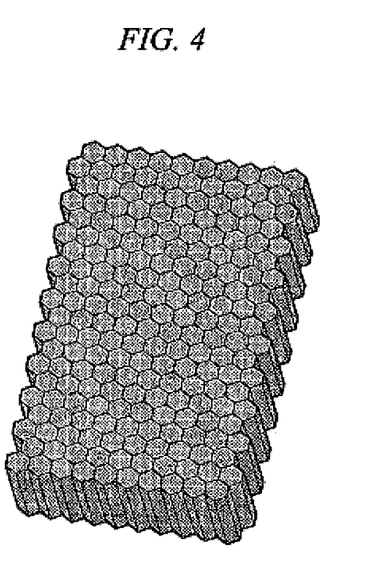
FIG. 4 is a schematic side view of a magnetizer having an array of magnetizing cores.

Alternatively, all hexagonal magnetization zones can by magnetized simultaneously by a customized magnetizer shown in FIG. 4. The magnetizer of FIG. 4 has an array of hexagonal magnetizing cores which can be independently controlled. Using this magnetizer, each hexagonal magnetization zone can be magnetized to have a desired polarity.

In use, a user can use the cosmetic device 100 to dip a cosmetic composition from a cosmetic container, apply the composition to the skin, and massage the skin, as mentioned above. During the massage with the cosmetic device 100, the magnetic force from the anisotropic magnetic element 20 induces diamagnetism in active components of the composition, which facilitates the transdermal permeation of the active components.

The cosmetic device 100 can be manufactured as follows:

In a first step, a body 10 including a handle part 11 and a head part 12 is provided. The head part 12 is formed to have a substantially flat surface. The body 10 may be formed by injection molding of a resin material. The handle part 11 and the head part 12 may be either integrally or separately formed. In the latter case, the handle part 11 and the head part 12 are joined together by means of adhesive for example.

In a second step, an anisotropic magnetic element 20 is provided. The anisotropic magnetic element 20 may be formed from a rubber magnet such as a ferrite rubber magnet, or a neodymium rubber magnet. The anisotropic magnetic element 20 is magnetized by a magnetizer to have a honeycomb magnetization pattern including a plurality of regular hexagonal magnetization zones. The anisotropic magnetic element 20 may be magnetized using either a magnetizer having one hexagonal magnetizing core, or a customized magnetizer having an array of hexagonal magnetizing cores.

In a third step, the anisotropic magnetic element 20 is attached to the head part 12 of the body 10. Any appropriate adhesive or double-stick tape may be used for the attachment.

Optionally, a cover may be further provided to cover and surround the anisotropic magnetic element 20 within the head part 12 of the body 10. The material of the cover may be identical to or different from the material of the body, which does not affect the magnetic force from the anisotropic magnetic element 20.

EXAMPLES

The present invention is described in a more detailed manner by way of non-limiting examples.

Example 1

An anisotropic magnetic element according to Example 1 was prepared from a neodymium rubber magnet. The anisotropic magnetic element had a thickness of 0.5 mm. The anisotropic magnetic element was magnetized to exhibit a honeycomb magnetization pattern including a plurality of regular hexagonal magnetization zones in array.

Comparative Example 1

An anisotropic magnetic element according to Comparative Example 1 was prepared in the same way as Example 1, with the exception that the anisotropic magnetic element was magnetized to exhibit a linear magnetization pattern including a plurality of linear magnetization zones along the longitudinal direction of the element.

Table 1 below shows the detailed parameters of Example 1 (honeycomb magnetization pattern) and Comparative Example 1 (linear magnetization pattern).

TABLE 1

| magnetic pattern comparison | | |
|---|---|---|
| | Example 1 | Comparative Example 1 |
| Sample product area (mm$^2$) | 292.04 | 147.85 |
| Actual magnetized area (mm$^2$) | 222.58 | 59.33 |
| Effective ratio | 76% | 40% |
| Number of zones per sample | 21 | 26 |
| Actual area of individual zone (mm$^2$) | 23.37 | 5.70 |
| Actual magnetized area ratio in a pattern | 0.75 | 0.36 |

As shown in Table 1, the actual magnetized area of Example 1 was 3.75 times larger than that of Comparative Example 1. Since diamagnetic repulsion is basically proportional to the strength of the magnetic field, Example 1 was considered to improve the transdermal permeation.

In order to demonstrate the improved transdermal permeation according to Example 1 compared with Comparative Example 1, Franz-cell (static diffusion cell) tests were conducted to evaluate the residual amount of ER2947 (dipeptide available from L'ORÉAL) on ex vivo porcine skin. The Franz cell had an application area of 1.7 cm$^2$ and a cell receptor volume of 4 mL. The receptor fluid was phosphate buffered saline (PBS) with pH 7.4. The receptor fluid was stirred during the tests. The porcine skin is located between the donor compartment and the receptor compartment with the aforementioned application area of 1.7 cm$^2$. The temperature of the porcine skin was maintained to 32+/−1 degrees Celsius (° C.). The composition including 1% ER2947 (as a donor compound) was topically applied to the porcine skin by 5 mg/cm$^2$. The anisotropic magnetic elements of Example 1 and Comparative Example 1 were respectively suspended above the porcine skin. After the compound application of 16 hours, the porcine skin was removed, and then the stratum corneum (SC) was stripped. Then, the residual amount of ER2947 in the stratum corneum (SC) of the porcine skin was analyzed with LC/MS/MS (Liquid Chromatography/Mass Spectrometry/Mass Spectrometry). For comparison, the Franz-cell test without any magnetic element was also conducted in the same conditions.

Table 2 below shows the residual amount of ER2947 in the stratum corneum (SC) of the porcine skin.

TABLE 2

| | Residual amount of ER 2947 | |
|---|---|---|
| | Amount of ER2947 in Stratum Corneum (ng/cm$^2$) | Improvement Rate |
| Example 1 | 1258 | 2.19 |
| Comparative Example 1 | 990 | 1.72 |
| No magnet | 574 | 1 (baseline) |

As shown in Table 2, Example 1 shows 219% increased penetration efficacy compared with the result of no magnet. Table 2 also shows that the hexagonal magnetization pattern results in the more efficient transdermal permeation, comparted with the linear magnetization pattern.

It should be noted that the foregoing embodiments are merely intended for describing technical solutions of the present invention rather than limiting the present invention. Although the present invention is described in detail with reference to the foregoing embodiments, those skilled in the art should understand that they may still make modifications to the technical solutions recorded in the foregoing embodiments or make equivalent replacements to a part or all of the technical features thereof.

REFERENCE NUMERALS

100 Cosmetic Device
10 Body
11 Handle part
12 Head part
20 Anisotropic magnetic element

The invention claimed is:

1. A cosmetic device for delivering an active component into a skin, comprising:
a body including a handle part and a head part extending from the handle part; and
an anisotropic magnetic element located in or on the head part of the body, the anisotropic magnetic element comprising a rubber magnet formed from a plurality of magnetic particles dispersed in a rubber material at a loading of 60 vol % to 80 vol %, wherein the anisotropic magnetic element is magnetized to generate a magnetic field and to induce diamagnetism in the active component;
wherein the anisotropic magnetic element has a honeycomb magnetization pattern;
wherein the honeycomb magnetization pattern includes a plurality of hexagonal magnetization zones in array, each hexagonal magnetization zone has either N polarity or S polarity.

2. The cosmetic device according to claim 1, wherein the anisotropic magnetic element includes a neodymium rubber magnet.

3. The cosmetic device according to claim 1, wherein the anisotropic magnetic element has a magnetic flux density between about 50 gauss (G) and about 1500 gauss.

4. The cosmetic device according to claim 1, wherein the head part of the body includes a cover for covering the anisotropic magnetic element within the head part of the body.

5. A method for delivering an active component into a skin using a cosmetic device, comprising:
providing the cosmetic device, the cosmetic device including:
a body including a handle part and a head part extending from the handle part; and
an anistropic magnetic element located in or on the head part of the body, the anisotropic magnetic element comprising a rubber magnet formed from a plurality of magnetic particles dispersed in a rubber material at a loading of 60 vol % to 80 vol %, wherein the anisotropic magnetic element is magnetized to generate a magnetic field and to induce diamagnetism in the active component;
wherein the anisotropic magnetic element has a honeycomb magnetization pattern;
wherein the honeycomb magnetization pattern includes a plurality of hexagonal magnetization zones in array, each hexagonal magnetization zone has either N polarity or S polarity;
generating a magnetic field via the anisotropic magnetic element; and
inducing diamagnetism in the active component.

6. The method according to claim 5, wherein the plurality of hexagonal magnetization zones are magnetized by a magnetizer having an array of hexagonal magnetizing cores.

7. The method according to claim 5, wherein generating the magnetic field via the anisotropic magnetic element having a honeycomb magnetization pattern includes generating the magnetic field via an anisotropic magnetic element formed from a neodymium rubber magnet.

8. The method according to claim 5, generating the magnetic field via the anisotropic magnetic element having a honeycomb magnetization pattern includes generating the magnetic field via an anisotropic magnetic element including a cover for covering the anisotropic magnetic element.

9. A method for manufacturing a cosmetic device for delivering an active component into a skin comprising:
providing a body comprising a handle part and a head part extending from the handle part;

providing an anisotropic magnetic element configured to generate a magnetic field and to induce diamagnetism in the active component, the anisotropic magnetic element comprising a rubber magnet formed from a plurality of magnetic particles dispersed in a rubber material at a loading of 60 vol % to 80 vol %, having a honeycomb magnetization pattern including a plurality of hexagonal magnetization zones in array, each hexagonal magnetization zone has either N polarity of S polarity; and attaching the anisotropic magnetic element to the head part of the body so as to be located in or on the head part of the body.

10. The method according to claim 9, wherein the plurality of hexagonal magnetization zones are magnetized by a magnetizer having an array of hexagonal magnetizing cores.

11. The method according to claim 9, wherein providing the anisotropic magnetic element includes forming the anisotropic magnetic element from a neodymium rubber magnet.

12. The method according to claim 9, further comprising providing a cover for covering the anisotropic magnetic element.

* * * * *

UNITED STATES PATENT AND TRADEMARK OFFICE
CERTIFICATE OF CORRECTION

| | | Page 1 of 1 |
|---|---|---|
| PATENT NO. | : 11,191,936 B2 | |
| APPLICATION NO. | : 16/323480 | |
| DATED | : December 7, 2021 | |
| INVENTOR(S) | : W. Park et al. | |

It is certified that error appears in the above-identified patent and that said Letters Patent is hereby corrected as shown below:

In the Claims

| Column | Line | |
|---|---|---|
| 9 | 9 | change "polarity of" to -- polarity or -- |

Signed and Sealed this
Sixth Day of December, 2022

Katherine Kelly Vidal
*Director of the United States Patent and Trademark Office*